US007521201B2

(12) United States Patent
Stave et al.

(10) Patent No.: US 7,521,201 B2
(45) Date of Patent: Apr. 21, 2009

(54) BACTERIOPHAGES AS SELECTIVE AGENTS

(75) Inventors: James W. Stave, Bear, DE (US); George B. Teaney, III, Oxford, PA (US)

(73) Assignee: Strategic Diagnostics Inc., Newark, DE (US)

( * ) Notice: Subject to any disclaimer, the term of this patent is extended or adjusted under 35 U.S.C. 154(b) by 322 days.

(21) Appl. No.: 11/262,859

(22) Filed: Oct. 31, 2005

(65) Prior Publication Data
US 2006/0094076 A1 May 4, 2006

Related U.S. Application Data

(60) Provisional application No. 60/624,092, filed on Nov. 1, 2004.

(51) Int. Cl.
*C12Q 1/04* (2006.01)
(52) U.S. Cl. .................. 435/34; 435/29; 435/235.1; 435/239
(58) Field of Classification Search .................. None
See application file for complete search history.

(56) References Cited

U.S. PATENT DOCUMENTS

| 4,528,269 | A | 7/1985 | Sandine et al. |
|---|---|---|---|
| 4,861,709 | A | 8/1989 | Ulitzur et al. |
| 5,447,836 | A | 9/1995 | Wolber et al. |
| 5,498,525 | A | 3/1996 | Rees et al. |
| 5,510,243 | A | 4/1996 | Boyd et al. |
| 5,843,699 | A | 12/1998 | Strenkoski et al. |
| 5,849,515 | A | 12/1998 | Grant |
| 5,861,270 | A | 1/1999 | Nelis |
| 5,888,725 | A | 3/1999 | Sanders |
| 5,958,675 | A | 9/1999 | Wicks et al. |
| 6,063,590 | A | 5/2000 | Brenner et al. |
| 6,090,541 | A | 7/2000 | Wicks et al. |
| 6,306,621 | B1 | 10/2001 | Brenner et al. |
| 6,322,783 | B1 | 11/2001 | Takahashi |
| 6,479,280 | B1 | 11/2002 | Muyldermans et al. |
| 6,555,312 | B1 | 4/2003 | Nakayama |
| 6,555,331 | B1 | 4/2003 | Hyman et al. |
| 6,660,470 | B1 | 12/2003 | Sanders |
| 6,670,145 | B2 | 12/2003 | Brenner et al. |
| 6,861,230 | B1 | 3/2005 | Murphy et al. |
| 2003/0180319 | A1 | 9/2003 | Rapson et al. |
| 2004/0029250 | A1 | 2/2004 | Sulakvelidze et al. |
| 2004/0132127 | A1 | 7/2004 | Brenner et al. |
| 2004/0137430 | A1 | 7/2004 | Anderson et al. |
| 2004/0248199 | A1 | 12/2004 | Squirrell et al. |
| 2004/0248298 | A1 | 12/2004 | Schutz et al. |

FOREIGN PATENT DOCUMENTS

| WO | WO92/02633 | 2/1992 |
|---|---|---|
| WO | WO97/22713 | 6/1997 |
| WO | WO01/79528 | 10/2001 |
| WO | WO 03/025208 | 3/2003 |

OTHER PUBLICATIONS

Demczuk, Walter et al.; "Phage-Based Typing Scheme for *Salmonella enterica* Serovar Heidelberg, a Causative Agent of Food Poisonings in Canada,"; Journal of Clinical Microbiology; Sep. 2003; 41(9):4279-4284.

Favrin, Stacy J. et al.; "Application of a novel immunomagnetic separation-bacteriophage assay for the detection of *Salmonella enteritidis* and *Escherichia coli* O157:H7 in food,"; International Journal of Food Microbiology 85; (2003); pp. 63-71.

Favrin, Stacy J. et al; "Development and Optimization of a Novel Immunomagnetic Separation-Bacteriophage Assay for Detection of *Salmonella enterica*Serovar Enteritidis in Broth,"; Applied and Environmental Microbiology, Jan. 2001; 67(1):217-224.

He, Xiaoqing et al.; "Bacteriophage Lytic Patterns for Identification of Salmonellae, Shigellae, *Escherichia coli, Citrobacter freudii*, and *cloacae*,"; Journal of Clinical Microbiology, Mar. 1992; 30(3):590-594.

Kurtboke et al.; "Use of bacteriophage for the selective isolation of thermophilic actinomycetes from composted eucalyptus bark,"; Can J Microbiol. Jan. 1993; 39(1):46-51.

Kurtboke et al.; "Use of polyvalent phage for reduction of streptomycetes on soil dilution plates,"; J Appl Bacteriol. Feb. 1992; 72(2):103-11.

Menshikov et al.; "Use of bacteriophages as selective factors in bacteriological diagnosis of mixed infections,"; Klin Lab Diagn. Mar.-Apr. 1996; (2):50-1.

Pisciotta, John M. et al.; "Marine bacteria cause false-positive results in the Colilert-18 rapid identification test for *Escherichia coli* in Florida waters," Applied and Environmental Microbiology, Feb. 2002; 68(2): 539-544.

Bull, J. J. et al., "Dynamics of success and failure in phage and antibiotic therapy in experimental infections", *BMC Microbiology*, vol. 2 Nov. 26, 2002, 35.

Theron, J. et al., "A sensitive seminested PCR method for the detection of Shigella in spiked environmental water samples", *Water Research*, vol. 35, No. 4 Mar. 2001, 869-874.

*Primary Examiner*—Ralph Gitomer
*Assistant Examiner*—Amanda P Wood
(74) *Attorney, Agent, or Firm*—Kilpatrick Stockton LLP

(57) ABSTRACT

Compositions containing bacteriophages and methods of using bacteriophages in microorganism detection assays and microbial growth and plating media are disclosed. The lytic ability of these phages to control the growth of non-target populations provides superior sensitivity and specificity to detection assays and reduces false negative and false positive results. The removal of contaminating bacteria reduces the microbial competition for nutrients in the growth media thereby increasing the efficiency and productivity of the culture. The phage treatment of the sample increases the proportion of target microorganisms in the sample over contaminating bacteria thereby requiring less time for enrichment to obtain a significant signal improving overall signal to noise ratio in assays and providing for higher yield of end product in microbiological production systems.

31 Claims, No Drawings

BACTERIOPHAGES AS SELECTIVE AGENTS

CROSS REFERENCE TO RELATED APPLICATIONS

This application claims the benefit of U.S. Provisional Application No. 60/624,092, filed Nov. 1, 2004, which is incorporated herein by reference.

FIELD OF THE INVENTION

This relates to the field of microbiology and more particularly relates to the use of bacteriophages in microbiological assays and processes.

BACKGROUND OF THE INVENTION

Bacterial contamination is the major cause of food and water-borne infections in the world causing gastroenteritis, diarrhea, cramps, vomiting and often fever. In underdeveloped countries, these infections kill approximately 1.8 million people annually, most of whom are children. The Centers for Disease Control and Prevention (CDC) estimates that 76 million Americans become ill, more than 300,000 are hospitalized, and 5,000 people die from food-borne illnesses each year alone. After eating contaminated food, humans develop varying degrees of illness ranging from a short, mild gastrointestinal distress, such as that referred to as "food poisoning," to life-threatening disease. The most commonly recognized food borne infections are those caused by bacteria such as, *Salmonella, Listeria, Campylobacter, Staphylococcus aureus* and *E. coli* O157:H7. For example, *Salmonella* are found throughout the environment, particularly in the intestinal tracts of birds, reptiles, farm animals and humans. Illness in humans often results from the eating of undercooked meats, milk or eggs or from cross-contamination of other foods which are eaten without cooking.

Harmful diseases such as cholera and shigellosis may be transmitted by contaminated water and are caused by bacteria which can often be traced to sources along rivers and lakes. Much of the contamination can be traced to leaking and overflowing sanitary sewer systems, wastewater treatment facilities, leachate from septic tanks, and fecal matter associated with storm runoff from areas with high densities of wildlife, pets or livestock. The principle bacterial pathogens that have been shown to cause human intestinal disease associated with drinking water are: *Salmonella typhi* (Typhoid fever) *Salmonella paratyphi-A* (paratyphoid fever); other *Salmonella* species (salmonellosis, enteric fever); *Shigella dystenteriae, S. flexneri,* and *S. sonnei* (bacillary dysentery); *Vibrio cholerae* (cholera); *Leptospira* spp., (leptospirosis); *Yersinia enterocolitica* (gastroenteristis); *Francisella tularensis,* (tularemia); *Escherichia coli* (gastroenteritis); and *Pseudomonas aeruginosa,* (various infections). Because of the seriousness of the diseases caused by water-borne bacteria and the importance of water as a natural resource, levels of "indicator" bacteria called coliform bacteria are often monitored. These indicator bacteria usually are harmless, but there are a few exceptions. Certain strains of *E. coli* have been associated with gastrointestinal infections in adults, known as traveler's diarrhea, urinary tract infections, and newborn meningitis. Certain strains of *Klebseilla pneumonia* have been associated with gastrointestinal infections, pneumonia, hospital-acquired urinary tract infections, burn wound infections, and as secondary invaders in other respiratory infections. *Enterobacter* has been associated with hospital acquired urinary tract infections. *Citrobacter* has been associated with urinary tract infections, superficial wound infections, osteomyelitis, neonatal meningitis, and gastroenteritis.

Similarly, bacterial contamination in medical or biological diagnostic methods presents a problematic and expensive obstacle to such diagnostics. Bacterial contamination in a biological sample such as blood, saliva or tissue culture can greatly impair a satisfactory result from many biological assays. Common approaches include treating biological samples with very high doses of antibiotics often without satisfactory results.

Industrial bacterial fermentation is another commercial area affected by bacterial contamination. Industrial production of ethanol fuel in the United States in 2005 is estimated to be 4.4 billion gallons, up two fold from the previous year. Ethanol is produced primarily using yeast (*Saccharomyces*) fermentation, with corn being the predominant feedstock. Other organisms used to a lesser extent for ethanol production include the bacteria *Zymomonas mobilis*. Other feed stocks include sugar cane, rice straw, barley and wheat waste, potato waste, wood waste, municipal waste, and beverage industry waste. With such materials serving as feedstock, it is not surprising that most fermentations take place in the presence of significant bacterial contamination. *Lactobacillus* are the major contaminants in ethanol production and their presence and resultant lactic acid production reduces yeast growth and ethanol yield.

Similarly, amino acids produced by fermentation are predominantly lysine and glutamic acid (1 million metric tons collectively), with lesser amounts of threonine and tryptophan. This represents a 3.5 billion dollar market worldwide. The primary organism used for production is *Corynebacterium glutamicum*. Feed stocks for this process include corn wastes combined with waste products high in nitrogen. *Bacillus* spp. make up a considerable amount of the contaminants that can occur, and being rapid growers, compete with the *Corynebacterium* for nutrients. Other bacterial fermentation products include metabolites, vitamins, antibiotics and enzymes all produced within microorganism cultures that are susceptible to bacterial contamination.

Conventional methods for the detection of bacterial contamination employ non-selective or selective bacterial culturing, or enrichment, followed by plating the cultures on selective media for verification of suspect colonies. This approach is time consuming and can take several days before results are obtained. Alternative methods, utilizing immunoassay or nucleic acid-based detection technologies, are more rapid. However, these methods still require an enrichment step for production of a detectable signal. The length of time needed for sufficient enrichment is dictated by the growth rate of the target bacteria in the sample.

Most high sensitivity bacterial detection and enumeration methods require an overnight incubation. In addition, these methods often suffer from a lack of sensitivity or specificity or require expensive equipment or considerable technical expertise to perform. One particular problem with these methods is that, during the enrichment step, nearly all bacteria in the culture enjoy enhanced growth. The presence of large numbers of non-target bacteria in the enrichment culture causes interference with detection of the target bacteria, resulting in lack of sensitivity, cross-reactivity, false negative and false positive results. Scientists have attempted to reduce this problem by adding antibiotics to the enrichment cultures. However, the presence of antibiotics in the enrichment media decreases the growth rate of the target bacteria, lengthens the amount of time required to perform the assay and fails to eliminate cross-reactivity.

More recently developed bacterial detection assays combine an enriched bacterial culture with a lytic bacteriophage, a virus that specifically infects the target bacteria. Lytic phages are among the simplest and most abundant organisms on earth. Phages infect respective host bacteria and inject phage DNA. Within infected bacteria, phage DNA is replicated and then incorporated into new viral particles made by the bacterial host. New phage particles are then released from their host bacterial cells via a process known as "lysis," which kills the infected bacterial cell. Lysis allows subsequent phage infection of adjacent bacteria in a rapid, exponential pattern. In contrast to lytic phages, temperate phages bolster their bacterial host's virulence, resilience, and general capacity to proliferate. In the newly developed bacterial detection assays, lytic bacteriophage are labeled in some way and the presence of the label is detected when the phage infects target bacteria present in the sample. As with assays employing immunoassay or nucleic acid based detection systems, the assays utilizing bacteriophage as means for detecting target bacteria also suffer from the inability to deliver rapid, highly sensitive results caused by the length of time required to grow and enrich the target bacteria and the simultaneous expansion of non-target bacteria in the sample that interferes or cross-reacts with detection of the target bacteria.

Therefore, what is needed is a bacterial detection method that is highly sensitive for minute concentrations of a target bacteria in a sample, such as a toxic bacterial contaminant in food, water, environmental, medical, agricultural, veterinary, pharmaceutical or industrial fermentation preparations yet provides rapid detection without creating the opportunity for undesirable false positive and negative results, and bacterial production processes that enrich for the target microorganism and improve production yield.

SUMMARY OF THE INVENTION

The present invention addresses the problems described above by providing rapid, highly sensitive methods and compositions for the detection of one or more microorganisms in a sample. Also provided are methods and compositions for enriching growth or replication of one or more microorganisms of interest while reducing or preventing growth or replication of undesirable bacteria. Preferred microorganisms are bacteria and yeast. The preferred microorganism of interest is bacteria.

The compositions provided herein contain one or more lytic bacteriophages as selective agents to reduce, eliminate or control the growth of unwanted or undesirable bacteria without inhibition of the growth or replication of the microorganism of interest. In one embodiment, the composition contains a lytic bacteriophage adapted for storage prior to use in an enrichment, diagnostic or selective media. In another embodiment, the composition contains a panel or set of lytic bacteriophages specific for the unwanted or undesirable bacteria. In another embodiment, the composition includes one or more lytic bacteriophages in enrichment media for the propagation, growth or culture of one or more select microorganisms of interest. In another embodiment, the composition includes lytic bacteriophages in microbial plating media for the plating, streaking, identification, characterization, enumeration or isolation of one or more specific microorganism colonies. The compositions may be packaged in kits with nutrients, reagents, including antibiotics, or combinations thereof for the enrichment, plating, isolation, selection, identification, enumeration or detection of the microorganism of interest. The compositions are useful in the production of alcohol, amino acids (such as, for example, lysine), or other chemical, molecule, substance or product in bacteriological, yeast, or other microbiological culture from agricultural, industrial, waste or other natural or non-sterile feed stocks. The compositions and methods described herein are also useful for detecting disease in plants and animals.

The methods provided herein may employ one or more of the lytic bacteriophage compositions described herein during preparation, enrichment or plating of the target microorganism of interest to reduce or inhibit the growth of undesired bacteria. For example, the compositions may be used in an industrial fermentation system to reduce the growth of competing bacteria and enhance efficiency and/or yield during the industrial fermentation or other commercial production of large quantities of a desirable microorganisms such as yeast in a brewery or bakery or recombinant bacteria in a recombinant protein production facility.

In an embodiment of the detection methods provided herein, one or more bacteriophages are used during the enrichment step of an assay for detection of a microorganism target to reduce or inhibit the growth of contaminating bacteria and allow unimpaired growth of the target microorganism to be detected.

Antibiotics that do not impair the growth or enrichment of the target or desirable microorganism are optionally included in the compositions and methods provided herein. A combination of antibiotics and bacteriophage in the composition allows for the inhibition of two different types of non-target bacteria. For example, gram negative and gram positive bacteria. The speed and efficiency of any enrichment is dependent in part on the level and composition of competing bacteria present in the sample. The removal or reduction of contaminating bacteria reduces the competition for nutrients, and the level of inhibiting or interfering substances in the culture, thereby increasing the efficiency of the enrichment step of the overall process. The phage treatment of the sample in the detection method increases the ratio of target to competing bacteria in the sample, thereby requiring less time for enrichment to obtain a significant signal and improving the overall signal to noise ratio in the assay.

In a preferred embodiment, the bacteriophage composition contains one or more bacteriophages and one or more antibodies. Each can be selected to have a different type of specificity for non-target bacteria. When combined with a sample, the specificity conferred by the action of a specific antibody in concert with the bacteriophage in the detection method results in superior specificity and sensitivity.

In another embodiment of the detection methods provided herein, one or more bacteriophages are used during microbial plating to reduce growth of unwanted bacteria on plating media and enhance the ability to detect, identify, enumerate or characterize the target microorganism.

In yet a further embodiment, the present methods provide a way to reduce or eliminate cross reactivity in the assay and false positive results.

The bacteriophage compositions provided herein are preferably stabilized in a dry form as a component of a powdered media formulation. In another preferred composition, the bacteriophage are stabilized in a dry form and added to the enrichment media or plating media during reconstitution of the media prior to the introduction of microorganisms to be cultured or plated or prior to the introduction of sample to be analyzed for the presence of target microorganism or alternatively added directly to the sample. Alternatively, the bacteriophage are in a dry or liquid form and added at any time prior to or during the enrichment or plating process, preferably prior to the addition of microorganism or sample.

Accordingly, it is an object of the present invention to provide a highly sensitive method for the detection of a target microorganism or class of microorganisms in a sample.

It is another object of the present invention to provide a highly specific method for the detection of a target microorganism or class of microorganisms in a sample.

It is a further object of the present invention to provide a microorganism detection assay in which interfering non-target bacteria are prevented from growing, reduced or eliminated.

It is another object of the present invention to provide a rapid method for the detection of a target microorganism in a sample, particularly a target bacteria such as a food, water, environmental, industrial or medical contaminant.

It is an additional object of the present invention to provide a rapid method for the selective growth or replication of a desired microorganism in an enrichment media, process or culture.

It is a further object of the present invention to provide compositions for use during enrichment of a target microorganism, wherein the compositions contain one or more selective agents that inhibit, reduce or remove non-target bacteria without significantly reducing enrichment of the target microorganism.

It is another object of the present invention to provide a microbial enrichment media for the growth of a target microorganism while minimizing or preventing growth of non-target bacteria.

It is another object of the present invention to provide a method for preventing or reducing undesirable bacterial growth in industrial fermentation reactions.

It is another object of the present invention to provide improved microorganism detection methods with reduced false positive responses due to the inhibition of or reduction in the presence of cross-reactive or non-specifically reactive bacteria in the sample.

It is another object of the present invention to provide improved microorganism detection methods with reduced false negative responses due to the inhibition of or reduction in the presence of competing or interfering bacteria and increased productivity of the target microorganism.

It is another object of the present invention to provide a method and composition for reducing microbial competition in a growth media, thereby increasing the efficiency and speed of an enrichment process of a test method.

It is another object of the present invention to provide a microorganism detection kit containing detection reagents and an enrichment media component or panel of components for the rapid, sensitive and specific detection of a microorganism in a sample.

It is another object of the present invention to provide a bacteriophage composition that improves yield of product in an industrial microbiological production process.

These and other objects, features and advantages of the present invention will become apparent after a review of the following detailed description of the disclosed embodiments and claims.

DETAILED DESCRIPTION OF THE INVENTION

Methods and compositions for the detection and production of one or more microorganisms in a sample or process are described herein. Methods and compositions for enriching growth or replication of one or more microorganisms of interest while reducing or preventing growth or replication of undesirable bacteria are also described.

The compositions described herein may contain one or more lytic bacteriophages as selective agents to reduce, eliminate or control the growth of unwanted or undesirable bacteria in a sample without inhibition of the growth or replication of a microorganism of interest, and the methods described herein utilize the compositions to enrich the target or desirable microorganism during microorganism culturing. These compositions preferably increase the sensitivity and specificity of the detection and decrease the rates of false positive or false negative results.

Bacteriophages, or phages, are bacterial viruses that bind to a host organism carrying a specific binding receptor. Bacteriophages are employed in the compositions and methods described herein because they exhibit a high degree of specificity when binding and lysing host bacteria. There are several advantages to using phage over antibiotics. Phages only multiply in the presence of the host bacteria, and in the presence of an appropriate host they increase in concentration providing even greater deterrence to growth of unwanted microorganisms. Phages can be far more specific than antibiotics, and specific phages can be selected to target specific bacterial strains. Phages are active at low concentrations and are able to infect bacteria that are resistant to antibiotics. When compared with antibiotics, smaller concentrations of phage are needed over a shorter period of time to achieve the same amount of bacterial destruction. Therefore, bacteriophages are capable of eliminating contaminating bacteria more rapidly and effectively than standard antibiotics. In addition, phage preparations are very simple and inexpensive to prepare and are extremely stable. Compositions of phage have a long shelf life and production costs are low, making the use of phage financially viable.

Bacteriophage Compositions

The bacteriophage compositions provided herein contain one or more phage strains suitable for the infection and killing of undesirable or contaminating bacterial species and strains. In one embodiment, the composition contains an isolated lytic bacteriophage specific for one or more unwanted or undesirable bacteria that is adapted for storage prior to use in an enrichment or plating media. In another embodiment, the composition contains a panel or set of lytic bacteriophages specific for the unwanted or undesirable bacteria. In another embodiment, the composition includes one or more lytic bacteriophages in enrichment media for the propagation, growth or culture of one or more select microorganisms of interest. In another embodiment, the composition includes lytic bacteriophages in solid or semi-solid microbial plating media for the plating, streaking, isolation, selection, characterization, enumeration or identification of one or more specific microorganism colonies. In another embodiment, the composition includes lytic bacteriophages to control unwanted bacteria or other microorganisms in cultures of yeast, fungi or higher eukaryotic cells such as plant or animal cells.

Bacteriophages

The bacteriophages of the compositions provided herein include any lytic bacteriophage specific for a bacteria other than the target microorganism to be detected or enriched. As used herein the terms "bacteriophage", "lytic bacteriophage" and "phage" can be used interchangeably and refer to bacteria-specialized viruses that infect specific bacteria types and replicate within the bacterial host and ultimately destroy the bacterial cell while releasing numerous phage progeny into the medium. Non-lytic or temperate phages are also useful in the composition described herein provided that non-lytic or temperate phages have been modified to induce lysis or prevent growth of the host bacteria. A method for the modification of such phages is described in U.S. Patent Publication 2003/0180319.

A bacteriophage is specific for a bacterial cell when it infects the given bacterial cell and does not infect bacterial cells of other species or strains. The specificity of a phage for its host is determined at two levels. The first level of control involves the interaction of phage components with complementary elements on the bacterial cell surface, which determines the ability of the phage to bind to the cell and inject its DNA. There is substantial evidence that phage breeding, genetic engineering of fiber elements, and hybridization, can alter phage specificity at this level. The second level of control over specificity is during the events occurring within the bacterial cell, after injection of the phage DNA. Therefore, the bacteriophage contained in the compositions described herein include genetically modified or recombinant phage that have been altered to increase binding affinity, infectivity, burst size, multiplicity of infection (moi) or lytic ability for the bacteria to be removed from a sample or culture.

Specific phages for over 100 bacterial genera have now been isolated (Ackermann, 1996 *Arch Virol.* 141(2):209-18.), and they have been found virtually everywhere that they have been sought. A great number of phages have been identified that infect different strains of *E. coli*. Over 20,000 strains of bacteria (with 7000 being *Salmonella*) have been evaluated for phage identification (He and Pan, 1992, *J Clin Microbiol* 30(3):590-4). A set of phages specifically targeting *Citrobacter* and *E. coli* but not *Salmonella* have also been described, demonstrating that a panel of phage can be assembled to target a specific set of organisms.

For the eradication of a given bacteria, a bacteriophage is selected that is capable of infecting the bacterial cell, replicating within the bacterial cell and lysing the bacterial cell. A wide variety of bacteriophages are available for any given bacterial cell, for example, from the American Type Culture Collection (ATCC, P.O. Box 1549 Manassas, Va., USA) or by isolation from natural sources that harbor the host cells. A list of phage types is published as the Catalogue of Bacteria & Bacteriophages. (American Type Culture Collection, Rockville, Md. 1989). Similar microorganism depositories publish equivalent data. This data is useful for the identification of bacteriophage reagents to be included in the compositions and methods described herein.

Besides exhibiting specificity and anti-microbial activity, phages have the ability to produce substantial self-amplification in a short amount of time. Under optimum infection and host growth medium conditions, a given phage/bacterium combination gives rise to a consistent number of phage progeny. For the detection of a particular bacterial cell, a bacteriophage is preferably used that gives an optimal or maximal burst size, that is the number of progeny produced per cell. Preferably the burst size from a lysed bacterial cell is from about 10 to 10,000 progeny phage particles from a single infected cell. High burst sizes are preferred in order to increase the rate of infection of a sample to remove contaminating bacteria more rapidly. The preferred burst time of the phage included in the compositions and methods described herein is from two minutes to four hours. Short burst times are preferred for faster destruction of contaminating bacteria. A single bacterial cell may be infected by multiple phage particles (multiplicity of infection, m.o.i.), and the phage burst depends on the multiplicity. To produce high yields, an m.o.i. of 10 is generally used. Higher m.o.i. are preferred because they result in more efficient lysis at lower concentrations of unwanted bacteria.

An example of a candidate phage to be included in the composition described herein is phi29 of *B. subtilis* because it gives a burst of 1,000 in a 35-minute life cycle. Similar phages with high burst size and short life cycle are preferred. Different types of bacteriophage may be obtained from commercial sources or from biological depositories such as the American Type Culture Collection (ATCC) or the Deutsche Sammlung von Mikroorganismen und Zellkulturen GmbH, (DSMZ), Braunschweig, Germany, the German National Resource Centre for Biological Material. Such bacteriophages include, but are not limited to, Actinoplanes/Micromonospora phages (Ap3, Ap4, Mm1, Mm3, Mm4, Mm5, phiUW 51); Amycolatopsis phages (W2, W4, W7, W11); *Bacillus* phages (GA-1, Phi 29, SPβ); Cellulomonas phages (O2, O3, O5, O6, O8, O11, O13); *Escherichia* phages (lambda, M13, M13, mp18, MS2, Mu, P1, PhiX174, Qβ, R17, T1, T2, T3, T4, T5, T6, T7, U3); *Lactococcus* phages (P001, P008); *Methanothermobacter* phage (psi M2 (ΨM2)); *Nocardia/Rhodococcus/Gordonia* phages (N4, N5, N13, N18, N24, N26, N36); *Nocardioides* phages (X1, X3, X5, X6, X10, X24); *Nocardiopsis* phages (D3, D4); *Promicromonospora* phages (P1, P2, P3, P4); *Pseudomonas* phages (Psp1, Psp2, Psp3, Psp4, Psp5); *Pseudonocardia* phage (W3); *Saccharomonospora* phages (Tm1, Tm2, Tm3); *Saccharopolyspora* phages (Mp1, Mp2); *Saccharothrix* phage (W1); *Sporichthya* phage (Sp1); *Streptomyces* phages (P23, P26, S1, S2, S3, S4, S6, S7, SH10, phi A. streptomycini III, phi8238, phiC31); *Terrabacter* phages (T1, Tb2); *Tsukamurella* phage (Ts1)

Other bacteriophages with a high level of specificity can be developed by screening samples using methods described in U.S. Pat. No. 6,322,783, which is incorporated herein by reference. Phages specific for particular bacteria can also be selected using routine techniques in the laboratory due to the ability of the phage to rapidly mutate, thereby producing host range mutants.

Phage Isolation

Because bacteriophages are specific to a particular species or strain of bacteria, they are typically found in association with their specific host bacteria. Bacterial sources of phage include but are not limited to samples of sewage; feces; soil; ocean depths; hot springs; wastes such as from hospitals, farm yards, and laboratories; food processing; meat packing and stockyards; and agricultural and industry processes. Phages also can be isolated from rivers and lakes, ponds, wells, water tables, as well as other water sources (including salt water). Water sources near likely sites of contamination are also preferable sources.

The procedures for isolating phage are as follows. Generally the sample suspected of containing a bacteriophage is filtered first and then enriched. In a culture containing a host bacteria, a sample is centrifuged and the supernatant is separated and passed through a micropore filter, such as those filters commercially available from the MILLIPORE® company, with pores small enough to prevent the passage of bacteria (approximately 0.45 μm to 0.2 μm) but large enough to permit the passage of phage. The filtered supernatant is then mixed at different dilutions with a pure culture of the specific host bacteria. The dilutions of bacteria and supernatant are spread on a nutrient agar plate or other solid nutrient substrate for bacterial culture. After about 8 to 24 hours, a bacterial lawn is evident with round clear spots, called plaques. Each plaque contains many million phage particles, all progeny of one phage which was immobilized on the agar. A sterile toothpick, or other similar device, is inserted into one plaque and transferred to a fresh culture of the bacteria in liquid nutrient medium. In this manner, a homogeneous stock of the phage clone is cultured and the phage may be studied in further detail or used for applications such as, but not limited to, bacterial selection and detection assays and production processes.

Individual bacteriophage strains (i.e., monophages) are propagated and then tested for activity against multiple bacteria strains to select phage with specificity for the desired bacterial strains. When attempting to control the growth of a wide variety of bacterial species and strains, efforts are made to select phages that are lytic and specific to more than one bacterial strain. It is also possible to select appropriate phages based upon the sequences of DNA or RNA encoding proteins involved in the binding and/or entry of phage into their specific host, or based upon the amino acid sequences or antigenic properties of such proteins.

Phage Formulations

Phage compositions can take the form of relatively crude lysates of bacterial cultures or highly purified virus preparations. Phage can be formulated in various ways for storage and shipping. In one embodiment, the phage is stabilized in a dry form and included as a component of a powdered media formulation, alone or incorporated into a powder that contains other substances such as culture media, excipients, bulking agents, etc.

In another embodiment, phage are freeze-dried or lyophilized into a dry powder and added to the enrichment media as a supplement during reconstitution of a powdered media or added later during the enrichment process if desired. Phages may be stored dried or freeze-dried on filter paper or as a dried or freeze-dried suspension, which can make shipping easier. Most phage can be freeze-dried in skim milk (e.g., 20%). Many methods for freeze drying phage have been described and are well know in the art. (See, for example, T. Kieser et al. PRACTICAL STREPTOMYCES GENETICS, published by the John Innes Foundation, ISBN 0-7084-0623-8, Chapter 12) Phage are also available in a liquid form or suspension.

In another embodiment, the phage is in a liquid form and is combined with media by spraying onto a media powder and mixed for even distribution or the liquid phage is combined with liquid media and mixed. The liquid phage is present alone in an aqueous solution alone or in solution with other substances such as sugars, polymers, proteins, salts, buffers, or detergents.

The media with which the bacteriophage is combined can be in liquid, solid or semi-solid form or incorporated into a media-based film such as Petrifilm™ plates (3M, St Paul, Minn.).

In another embodiment, liquid suspensions of phage are frozen with or without cryoprotectant. Liquid compositions are preserved refrigerated at, for example, approximately +4° C., or cryoprotected in glycerol (e.g., 50%) and frozen in liquid nitrogen at about −80° C. Phage are recovered from freeze-dried or thawed liquid nitrogen vials as follows. Actively growing cultures of host bacteria are prepared for about one to 48 hours and the freeze-dried phage aseptically rehydrated with nutrient medium. The bacterial cultures are plated on a nutrient agar plate as a soft-agar host overlay (for example, as described in Adams, M. H. (1959) BACTERIOPHAGES, Interscience Publishers, Inc., New York) and drops of rehydrated or thawed phage are added to the host-agar layer. Plates are grown overnight and the phage are isolated from the resulting plaques using conventional methods.

To propagate phage, plates are prepared with the soft-agar/host overlay as above and the surface is covered with approximately 0.5 ml of the concentrated phage. Alternatively, the phage is added directly to the melted agar/host before pouring over the plates. For larger amounts, large size T-flasks can be prepared with the recommended agar, and approximately 12 ml of melted soft-agar/host poured over the surface. Phage is then allowed to run over the hardened surface. Phage may also be added directly to melted soft-agar before pouring as described above. After about 24 hours of incubation, the soft agar is scraped off the surface of the agar plates and centrifuged at about 1,000 rpm for approximately 25 minutes to sediment the cellular debris and agar. The supernatant is passed through a filter, preferably a 0.45 µm to 0.22 µm filter, and the filtrate is stored at approximately 4° C. to 8° C. Lysates remain viable under refrigeration for long periods.

Phage can also be propagated by growing host bacteria in broth cultures, inoculating with phage, incubating for sufficient time to cause lysis of bacterial cells and filtering the resulting lysate through a 0.45 to 0.2 µm filter.

Phages are also preserved within cultures of lysed bacteria and cryopreserved for later reconstitution in nutrient growth medium. Lysed bacterial cultures are cryopreserved, for example with glycerol (e.g., 10-50%) or DMSO (e.g., 5%), in nutrient media and stored in liquid nitrogen. Lysed bacterial cultures may also be freeze-dried and cryopreserved in skim milk (e.g., 20% ), or a sucrose solution (e.g., 12%) in nutrient medium. Frozen bacterial lysates are rapidly thawed in a water bath at approximately 37° C. and the entire aliquot is inoculated into fresh medium. Methods for growth, lysis and storage of bacterial cultures harboring phage particles are well known in the art.

Phage preparations can be monovalent, in that they contain one type of bacteriophage, or polyvalent, wherein they contain more than one type of phage. Polyvalent preparations, also known as phage cocktails or phage panels, are formulated to include several phage species to target more than one bacterial strain or species. The combination in a phage cocktail may include several phages targeting different bacterial strains or can have broader actions by containing phages directed to several bacterial species. Phage cocktails may include a mixture of phages specific for various unrelated bacterial species to eliminate contaminating bacteria in a culture designed to enrich a target bacteria.

In one embodiment, a combination of phage is used where the combination contains phage specific for *Enterococcus* spp., *Escherichia* spp., *E. coli*, *Pseudomonas* spp., *Shigella* spp., *Bacillus* spp., *Enterobacter* spp., *Citrobacter* spp., *Proteus* spp., *Klebsiella* spp., *Lactobacillus* spp., and *Staphylococcus* spp. In this embodiment, the mixture lacks phage specific for *Salmonella* spp. and therefore is useful for enriching a sample for *Salmonella* when grown in nutrient media with this phage cocktail as an additive. Similar phage preparations can be designed for specific enrichment of a desired target bacteria by including phage that are specific to undesired bacteria and omitting phage specific for the target bacteria. Phage specific for bacteria genera can be combined to create a broad-spectrum antibacterial mixture. In a preferred embodiment for detection of pathogenic bacteria in food samples, phage are selected that are specific for members of the family of Enterobacteriaceae other than the target of the detection method.

Phage cocktails may be custom tailored to the bacteria that are prevalent in certain samples. In a preferred embodiment, phage are selected that are specific for the most predominant or highest concentration bacteria in the sample other than the microorganism to be detected. The most prevalent bacteria are isolated from a high dilution of a particular sample and tested for susceptibility to various bacteriophage strains in a manner analogous to antimicrobial susceptibility testing. Once the bacterial profile of a sample is known and the phage susceptibility profile is determined, the appropriate phage cocktail is formulated for a particular sample to prevent the growth of the competing bacteria and enrich for the target organism.

In another embodiment, phage specific for bacteria genera may be combined to create a broad-spectrum antibacterial mixture for use when culturing yeast, fungi or higher eukaryotic cells such as plant or animal cells.

Phage concentrations in solid, semi-solid or liquid media or culture useful for the control of undesirable microorganisms in the compositions and methods described herein are preferably $10^3$ to $10^{12}$ plaque forming units per mL (PFU/mL).

In another embodiment, antibiotics are incorporated in media specific for an entire class of microorganisms from which the target microorganism is excluded, such as gram positive bacteria (such as, but not limited to, *lactobacillus* and *staphylococcus*) and phage are added to the media to remove gram negative bacteria cross-reactive with the particular detection reagent or method employed.

Detection Assay Kits

A kit for detecting a bacterial cell in a sample is also provided herein. The present kits may be used in methods such as PCR, BAX, Biochemical identification such as API, microidentification, fatty acid analysis and enzyme based tests such as COLILERT® (Idexx Laboratories, Inc.). The kit includes microorganism growth media and one or more bacteriophage specific for potentially competing, interfering or undesirable bacteria. The bacteriophage preparation is an integral component of the growth media, is a separate component immobilized on a solid substrate, or is provided as a separate liquid or powdered solid additive. Exemplary solid substrates are fibers, fibrous filters, membrane filters, and particles such as latex beads, colloidal gold, magnetic particles, silica particles, and other particles known in the art. The kit optionally includes printed instructions, one or more positive controls, one or more negative controls or combinations thereof.

In addition, the kit optionally includes reagents and means for separating one component in the sample from another. Means for separation include, but are not limited to, liquid-liquid extraction reagents and equipment as well as solid substances such as filters, latex beads, colloidal particles including bacteria, magnetic particles, means for centrifugation, solid substances having defined characteristics such as electronic charge, porosity and hydrophilic/hydrophobic surfaces, lateral flow devices, immunochromatographic devices, and others well known in the art.

Reagents useful for separations include, but are not limited to, antibodies, nucleic acid molecules, streptavidin, avidin, biotin, carbohydrates, proteins, peptides, protein A, protein G, small molecules and other binding ligands well known in the art. Such reagents and means for separating may be directed towards, and useful for separating, any component of the entire test process including sample preparation, enrichment, growth or replication, and testing. Such reagents and means for separation, and combinations thereof, are well known to those skilled in the art and are contemplated by the compositions and methods described herein. Means for performing separations in kits designed to detect components of microorganisms using antibodies, nucleic acid molecules and other binding ligands are well known in the art and are within the scope of the compositions and methods described herein.

The performance of a comprehensive biochemical analysis generally requires the molecule to be isolated in pure form from other molecules in an extract from a biological sample, then characterized and analyzed for its function. Biochemical assays may characterize a molecule, quantitatively or semi-quantitatively, and detection assays may range from the simple type of assays provided by spectrophotometric measurements, enzyme activity and gel staining to determine the concentration and purity of proteins and nucleic acids, to more detailed assays.

Reagents for detecting the organism of interest are optionally provided with the kit and include detectable ligands such as antibodies or nucleic acid sequences specific for the organism to be detected or enzyme or substrate or other chemical or biochemical molecules or indicators. The ligands can be conjugated to a detectable marker that is calorimetric, radioactive, fluorescent, chemiluminescent, bioluminescent, electrochemical, enzymatic or metabolic, or other markers routinely used in the art. Such reagents are well known to those skilled in the art.

Methods of Using the Bacteriophage Compositions

The methods provided herein employ one or more of the lytic bacteriophage compositions described above during enrichment or plating of a desirable or target microorganism of interest to reduce, inhibit, or eliminate the growth of undesired bacteria.

In one embodiment, the compositions are useful in an industrial fermentation system to reduce the growth of competing bacteria and enhance efficiency and yield during the industrial fermentation or other commercial production of large quantities of a desirable organism such as yeast in a brewery or bakery, or recombinant bacteria in a recombinant protein production facility, or eukaryotic cells or tissues in an industrial or pharmaceutical process. Enhanced microorganism production results in enhanced production of the product produced by that organism. A list of common products produced using microorganism is set forth below in Table 1. The microorganism enrichment methods provided herein are particularly useful when the feedstock or input material is not sterile and therefore contains a contaminating microorganism. For example, enrichment of yeast (such as, but not limited to, *Saccharomyces* or *Zymomonas mobilis*) in a feedstock-containing fermentation reaction enhances ethanol production. Other feed stocks include sugar cane, rice straw, barley and wheat waste, potato waste, wood waste, municipal waste, and beverage industry waste. With such materials serving as feed stocks it is not surprising that most fermentations take place in the presence of significant bacterial contamination. *Lactobacilli* are the major contaminants in ethanol production and their presence and resultant lactic acid production reduces ethanol yield and reduces yeast growth.

The amino acids produced by fermentation are predominantly lysine and glutamic acid (1 million metric tons collectively), with lesser amounts of threonine and tryptophan. This represents a 3.5 billion dollar market worldwide. The primary organism used for production is *Corynebacterium glutamicum*. Feed stocks for this process include corn wastes combined with waste products high in nitrogen. *Bacillus* species make up a considerable amount of the contaminations that can occur, and being rapid growers, compete with the *Corynebacterium* for nutrients.

TABLE 1

| Industrial Fermentation Products | |
|---|---|
| Metabolite | Produced by |
| Citric Acid | *Aspergillus niger* |
| Acetone and butanol | *Clostridium acetobutyricum* |

TABLE 1-continued

Industrial Fermentation Products

| | Produced by |
|---|---|
| Riboflavin | *Ashbya gossipii* |
| Vitamin B12 | *Pseudomonas denitrificans* |
| | *Propionibacterium shermanii* |
| Dextran | *Leuconostoc mesenteroides* |
| Xanthan gum | *Xanthomonas campestris* |
| Antibiotics and related | |
| Penicillin | *Penicillium chrysogenum* |
| Erythromycin | *Streptomyces erythreus* |
| Streptomycin | *Streptomyces griseus* |
| Cephalosporin | *Cephalosporium acrimonium* |
| Griseofulvin | *Penicillium griseofulvin* |
| Cyclosporin | *Tolypocladium inflatum* |
| Gibberellin | *Gibberella fujikuroi* |
| Enzymes | |
| Amylases | *Aspergillus oryzae* |
| Glucamylase | *Aspergillus niger* |
| Cellulase | *Trichoderma reesii* |
| Invertase | *Saccharomyces cervisiea* |
| Lactase | *Kluyveromyces fragilis* |
| Lipase | *Saccaromycopsis lipolytica* |
| Pectinase and Protease | *Aspergillus* species |
| Protease | *Bacillus* species |
| Microbial rennet | *Mucor pusillus* and *Mucor meihei* |

It will be understood by those skilled in the art that, when used in an enrichment method for production purposes, such as industrial fermentation, recombinant production or other commercial production, the sample to which the bacteriophage composition is added is an extremely large sample such as the contents of a production vat, vessel, reactor (such as a microbiological reactor for the production of a biological product using bacteria or yeast), or fermentor.

Alternatively, the bacteriophage composition is used in a method for the detection of a target microorganism in a sample. In one embodiment, one or more bacteriophages are used during the enrichment step of a method for detection of a bacterial target to reduce or inhibit the growth of contaminating bacteria and preferentially allow the growth of the target bacteria to be detected.

In another embodiment, one or more bacteriophages are used during microbial plating to reduce growth of unwanted bacteria on the plating media and enhance the ability to isolate, detect, enumerate or identify the target microorganism. Suitable plating media include both solid and/or semi-solid media.

Target Cell populations

The methods described herein are useful for the detection, growth, replication, enrichment, isolation, characterization, enumeration or identification of any microorganism of interest. Those skilled in the art will appreciate that there is no limit to the range of target microorganism populations other than the availability of the necessary specific phage to remove competing or undesirable contaminants. Preferably, the target microorganisms are bacteria. A compendium of bacteria for which the methods and compositions are useful is Bergey's Manual of Systematic Bacteriology (Lippincott Williams & Wilkins). Target bacterial cells contemplated by the present methods include, but are not limited to, bacterial cells that are food, water, or environmental contaminants, pathogens of agricultural, medical or veterinary significance, and bacterial cells useful in pharmaceutical, industrial or commercial processes. Specific target bacterial cells include, but are not limited to, all species of *Salmonella*, all strains of *E. coli*, including, but not limited to *E. coli* O157:H7, all species of *Listeria*, including, but not limited to *L. monocytogenes*, coliforms, all species of *Legionella*, and all species of *Campylobacter*.

Pathogenic bacteria may also include but are not limited to *Acinetobacter calcoaceticus, Actinomyces israelii, Bacillus* spp. (*Bacillus anthracis, Bacillus subtilis, Bacillus cereus*), *Bordetella pertussis, Borrelia burgdorferi, Borrelia recurrentis, Brucellae (Brucella melitensis, Brucella abortus, Brucella suis, Brucella canis), Costridium* spp. (*Clostridium tetani, Clostridium perfringens) Corynebacterium diphtheriae, Campylobacter jejuni, Chlamydia pneumoniae, Enterococci (Enterococcus faecalis), Escherichia coli, Eubacterium alactolyticum, Enterobacter* spp. (*Enterobacter cloacae*), *Francisella tularensis, Flavobacterium meningosepticum, Helicobacter pylori, Klebsiellae (Klebsiella pneumoniae), Legionella* spp. (*Legionella pneumophilia*), *Leptospira interrogans, Mycobacterium tuberculosis, Mycoplasma pneumoniae, Moraxella catarrhalis, Moraxella lacunata, Neisseria gonorrhoeae, Neisseria meningitidis, Proteus,* (*Proteus mirabilis, Proteus vulgaris*), *Pseudomonas aeruginosa, Providencia alcalifaciens, Providencia stuartii, Providencia rettgeri, Rickettsia prowazekii, Salmonellae (Salmonella choleraesuis, Salmonella typhimurium, Salmonella enteritidis typhi), Serratia* spp., *Staphylococci,* (*Staphylococcus aureus, Staphylococcus epidermidis*), *Shigella* spp. (*Shigella dysenteriae*), *Spirillum minus, Streptococci, Treponema pallidum, Ureaplasma urealyticum, Vibrio* spp. (*Vibrio cholerae, Vibrio vulnificus*), *Xanthomonas maltophilia,* and *Yersinsia* spp (*Yersinia pestis*).

Target bacterial cells contemplated by the present methods also include, but are not limited to, bacterial cells found to be contaminating systems of commercial significance, such as those used in commercial fermentation industries, ethanol production, antibiotic production, amino acid production, pharmaceuticals, wine production, pharmaceutical production, waste treatment, water treatment, bioremediation, etc. Such bacteria include, but are not limited to, organisms such as *Lactobacillus* spp., *Corynebacterium* spp., *Brevibaacterium* spp., and *Acetobacter* spp. during ethanol production. Other examples of bacteria include those listed in W. Levinson et al., MEDICAL MICROBIOLOGY & IMMUNOLOGY, McGraw-Hill Cos., Inc., 6$^{th}$ Ed., pages 414-433 (2000). All bacterial cultures are grown using procedures well known to those skilled in the art.

It will be understood by those skilled in the art that the term "target microorganism" means a single species, isolate or strain as well as groups or families of organisms. For example, the method is useful for detection of *Salmonella enteritidis* as well as all *Salmonella*.

The methods provided herein for detection of a target provide high detection sensitivity in a short amount of time without the need for lengthy cultural enrichment. For example, the present methods can provide for the detection or quantification of less than about 100, less than about 50 or less than about 10 bacterial cells in a sample. Preferably the present methods can provide for the detection or quantification of less than about five, less than about four, less than about three, or less than about two bacterial cells in a sample. Most preferably, the methods can provide for the detection and quantification of a single bacterial cell in a sample.

A bacterial generation time is defined by the bacterial growth rate under standard nutritional conditions (culture medium, pH, temperature, etc.) during the exponential growth phase. The target bacteria preferably have a generation time of 10 minutes to 36 hours. Bacteria having shorter generation times within this range are preferable, thereby reducing the time required for the enrichment step in the detection assay. However, the present invention is particularly useful for target bacteria with long generation times because it prevents or inhibits the growth of faster growing non-target microorganisms.

Use of Bacteriophage as a Selection Agent in Culture Media

When used as a selection agent in culture media, bacteriophage is added to the growth media similar to any growth additive that would be routinely added. Use of bacteriophage rather than antibiotics reduces the incubation time needed because the bacteriophage does not impair the growth of all bacteria including the target while destroying contaminating bacteria. As used herein, contaminating is defined as an organism or agent present in the culture that is not intended, or desired to be present before, during or at the termination of the culture period. Non-selective, rapid-acting growth media are traditionally avoided in many applications because the potential for contaminating species to overtake the culture is a concern. Bacteriophage treatment permits use of rapid acting growth media in the absence of antibiotics, thereby encouraging rapid growth while still preventing overgrowth by contaminating bacteria.

In one embodiment samples are enriched in the presence of approximately $1 \times 10^7$ PFU/ml of each bacteriophage for about 40 hours at 35° C. although the temperature may vary. The number of plaque forming units may be adjusted higher or lower to achieve more or less infection. The incubation time is preferably less than 40 hours, preferably less that 18 hours, preferably less than 10 hours, preferably less than 6 hours, or preferably less than 2 hours. Incubation times may be adjusted depending on the burst time.

In accordance with the method, bacteriophage cocktails are added to either small volume cultures or to large scale industrial fermentation reactions. Because bacteriophage multiply in the presence of the host bacteria, high concentrations are not required in the large-scale fermentation cultures thereby reducing costs associated with maintaining a contaminant-free culture.

The addition of bacteriophage is used to control a broad range of indigenous microflora in bacterial culture. Treatment with a panel of bacteriophage removes a mixture of competing bacteria from the nutrient medium. A broad spectrum combination of bacteriophages can dramatically reduce the total number of contaminating bacteria from a sample thereby permitting greater access to nutrients for the target bacteria to be detected and less exposure to potentially inhibiting substances produced by the undesirable bacteria. This optimizes the growth conditions for the target bacteria permitting faster replication and shorter time to yield positive detection.

Other advantages of the present methods are the reduction of false negative and false positive responses by the detection assay. In the presence of high concentrations of competing microorganisms in a culture, the target bacteria may never reach a concentration that is high enough to be detected by the assay method, regardless of the length of time permitted for enrichment, resulting in a false negative test. It is not essential that the target bacteria be the only organism in the sample or even the organism at the highest concentration. It is sufficient that the productivity of the target bacteria be such that the concentration is detectable by the assay method. The use of phage to inhibit or retard the growth of competing microorganisms in the enrichment improves target bacteria productivity and reduces false negative responses by the test method. Phage also provides for significant reduced enrichment time to get to a detectable level and enables remedial action sooner and minimizes cost.

False positive responses are also reduced by employing the present methods. It is known that false positive reactions can occur when a detection assay exhibits cross reactivity, or non-specific reactivity to non-target bacteria. For example, false positive responses arise when antibodies are employed in the detection assay that bind the target organism and also cross-react with non-target bacteria present in the sample. Phage have binding specificity profiles to bacteria that are different than the specificity profiles of antibodies. Where antibodies, nucleic acid molecules, chemical, biochemical, enzymatic or other means that are used to detect the target organism exhibit cross reactivity or non-specific reactivity to non-target organisms, phage can be used to reduce the concentration of the offending organism to below detectable limits and thereby reduce false positive responses.

Detection Assays

The methods described herein provide for the detection, identification, enumeration or characterization of target bacteria in a sample such as, but not limited to, *E. coli* O157:H7, *Salmonella* spp., *Legionella* spp., *Campylobacter* spp., coliforms, fecal coliforms, and *Listeria* spp. The methods reduce problems normally encountered when culturing bacteria prior to analysis, enriching for target cell populations, or minimizing competing species. In one embodiment, a sample is incubated in the presence of a bacteriophage mixture that is specific for and has the capability to lyse one or more undesirable bacterial species and is not specific for or does not lyse the target bacterial species. Following sample incubation with bacteriophage the presence of the replicated target bacterial cells are detected, identified, enumerated or characterized. General detection assays exist in the art and can be modified to incorporate the addition of a bacteriophage-mediated selection step. Examples of bacterial detection assays are found in U.S. Pat. Nos. 5,498,525; 6,555,331; 6,322,783; U.S. Patent Publication 2004/0137430; Blackburn 1993 *J. Appl. Bacteriol.* 75:199-214; Peplow et al. 1999 *Appl. Environ. Microbiol.* 65:1055-1060 and Swaminathan et al. 1994 *Annu. Rev. Microbiol.* 48:401-426. Preferably, the microorganism of interest is detected using immunoassay, PCR, chemical, biochemical, enzymatic or cultural methods.

Any bacterial detection, characterization or identification assay, or combination of assays may be used in the present methods. Many such bacterial assays are known in the art and many are commercially available. For assays in which the bacteria is a food pathogen, examples of such assays include, but are not limited to immunoassays such as the RAPIDCHEK *E. coli* O157, *Salmonella*, and *Listeria* tests commercially available from Strategic Diagnostics Inc. (Newark, Del.); the VIP *E. coli* test commercially available from Bio-Control Systems Inc. (Bellevue, Wash.); the REVEAL tests commercially available from Neogen Corporation, Lansing, Mich.; the IMMUNOCARD STAT! *E. coli* O157:H7 tests commercially available from Meridian Diagnostics, Inc., Cincinnati, Ohio; the OXOID *Listeria* Rapid Test commercially available from Oxoid Limited, Hampshire, England; the VIDAS ECO test or Vitek technology commercially available from bioMerieux Inc. (Hazelwood, Mo.); and the Unique *Salmonella* Assay commercially available from Tecra International Pty Ltd. (Chatswood, Australia).

Additional assays for characterizing or identifying food pathogenic bacteria include, but are not limited to, agglutination assays such as the REMEL *E. coli* O157 Latex from REMEL, Inc. (Lenexa, KS), REMEL *E. coli* H7 Latex from REMEL, Inc., and the REMEL *Salmonella* Latex from REMEL, Inc.; bacterial characterization kits such as the REMEL MicroID system from REMEL, Inc., and the bioMerieux api20E system from bioMerieux-Vitek. Inc.;

DNA polymerase chain reaction (PCR) tests such as the BAX *E. coli* O157:H7, *Salmonella* spp., and *Listeria* spp. tests from DuPont Qualicon Inc., Wilmington, Del.; motility tests for determining the presence and structure of types of flagella such as the H7 flagellates; and toxicology tests that identify the characteristics of toxins produced by a bacteria. Tests performed by outside services such as the H 1-58 Serotyping such as that performed by the *E. coli* Reference Center (Department of Veterinary Science at The Pennsylvania State University, University Park, Pa.) and the H Serology test, (also performed by the *E. coli* Reference Center), are also used for this purpose in some embodiments.

In some embodiments, the characterization and identification assay involves placing the microbial flora isolated from the primary cultural enrichment under secondary cultural conditions effective to indicate bacterial identity. In such instances, bacteria from the primary enrichment may be streaked directly upon several agar plates of high selectivity or placed in another highly selective medium. Because of the degree of selectivity of the medium, the subsequent growth of a colony alone can provide a basis for identifying a bacterial isolate.

Primary or secondary culture methods effective for indicating bacterial identity, include those containing specific chemical substances, enzymes or enzyme substrates that when acted on by specific bacteria, result in detectable changes such as a change in color, pH, redox potential, fluorescence, turbidity, luminescence, aggregation or other change, including chromogenic agar and broth many of which are commercially available and described in the DIFCO manual.

Some examples of agars for selecting, characterizing or identifying *E. coli* O157 bacteria include Cefixie-Potassium Tellurite Sorbitol MacConkey agar ("CT-SMAC"); available from Becton, Dickinson and Company, Sparks, Md.; and RAINBOW Agar O157, available from Biolog Inc., Hayward, Calif. Some examples of selective agars for enriching and identifying *Salmonella* bacteria include ASAP *Salmonella* plates (Available from AES Laboratoire, Combourg, France), Xylose Lysine Deoxycholate (XLD) plates and Brilliant Green Sulfadiazine (BGS) plates, both available from Becton, Dickinson and Company. Other examples of agars for characterizing bacteria include Eosin Methylene Blue (EMB), Phenol Red Sorbitol Agar, Blood Agar, and Luria Bertani Agar (LB), all available from Becton, Dickinson and Company. An example of selective agars for enriching and identifying Listeria bacteria is ALOA *Listeria monocytogenes* plates from AES Laboratoire, Combourg, France. The listing of examples of agars and media for selecting, characterizing, enumerating, or identifying bacteria is not limiting, and any environment that indicates, detects selects, characterizes, enumerates, or identifies bacteria is within the scope of the methods. The present methods contemplate the use of phage as selective agents in any and all culture steps in a process, as well as a direct means for detecting, identifying, typing, enumerating or characterizing bacterial cells arising from such steps The methods described herein, including cultural enrichment and detection, allow for the rapid detection of microorganisms such as bacterial cells. For example, the methods can be performed in less than about 48 hours, more preferably in less than about 32 hours, more preferably in less than about 16 hours and most preferably in about eight hours or less.

Enrichment of Bacterial Cultures in Detection Assays

All standard procedures for detecting microorganisms require an enrichment step of sample in growth media. The enrichment step amplifies the number of target microorganisms in the sample. The present method contemplates the use of bacteriophages as selective agents in microbiological media to inhibit the growth of certain non-target bacteria during enrichment. In a preferred embodiment, a panel of bacteriophage are used during enrichment to inhibit or kill competing organisms in an assay or test kit for microorganisms such as *Salmonella*, in food or *Legionella* or coliforms in water.

The enrichment step is optionally accompanied by an immuno-separation step, such as by using antibody-conjugated magnetic beads. Antibodies may also be fixed on a solid support to isolate the target microorganisms. Antibodies having specificity to surface receptors on the target microorganism are preferable. The antibodies preferably have minimal cross-reactivity with other microorganisms and are specific to one type of cell. However, in the event that an antibody is used that cross-reacts with other strains or species, treatment of the sample prior to detection with a panel of bacteriophage will prevent the growth of or remove any contaminating bacteria from the sample that cross-react with antibodies. For example, antibodies have been developed that are specific for *Salmonella*. Not all *Salmonella* antibodies are specific and some may cross-react with non-*Salmonella* cells. This problem is overcome by preventing the growth of cross-reacting non-*Salmonella* cells before detection by adding a panel of bacteriophage specific to the cross reacting non-*Salmonella* cells to the enrichment mixture.

During the standard enrichment process, non-target microorganisms may overgrow the target. It has been a common strategy to add a selection agent such as an antibiotic to the media to discourage the growth of non-target organisms. Examples of selection agents include antibiotics, dyes, bile salts, detergents, and other substances known to those skilled in the art. Unfortunately the addition of antibiotics inhibits the growth of non-target organisms but also may impair the growth of the target. Antibiotics that impair the growth of target bacteria are preferably absent in the methods described herein.

A particularly preferred method is one in which the total specificity of the overall method is determined by a combination of bacteriophage, antibiotics and the detection method (such as an immunoassay, biochemical test or PCR).

Increasing Signal in Bioluminescence Assays

Bioluminescence has perhaps the highest intrinsic sensitivity among biochemical detection methods. Expression of the bacterial luciferase (lux) gene can be detected at high sensitivity by measuring the light emitted by the cells expressing the gene in the presence of a suitable substrate. Several investigators have incorporated lux into a phage genome to express lux in a target bacterium (Loessner et al. 1996 *Appl Environ Microbiol.* 62(4):1133-40.; Duzhii et al. 1994 *Mol Gen Mikrobiol Virusol.* (3):36-8). Phage can be used in this manner to directly detect the target organism. In the present methods, phage can also be used in combination with this detection method, as with other detection methods, to improve the performance of the detection method as demonstrated by the following example.

The intrinsic sensitivity of bioluminescence assays is unsurpassed, but is often unrealized. Light detection down to the level of single photons is readily achieved, however limitations arise first in getting the emitted photons to the detector and second in distinguishing them from spurious background signals including phosphorescence. In complex samples, emitted photons are readily obscured by scattering or absorption by other sample components. Sample geometry is also a factor in efficiently delivering emitted photons to the detector. The emitted light will be most readily observed if the luciferase-expressing cells are separated from opaque components of the medium and potential sources of background and arranged in a thin layer with close optical coupling to the detector. Phage treatment of the sample decreases the non-infected, non-luminescent cells in the culture while promoting improved, faster growth of the luminescent target cells due to reduced nutrient competition.

Reduction of non-target cells in suspension culture reduces scatter of light by these cells. Lysis of non-target cells by bacteriophage reduces the noise in the assay thereby improving the signal to noise ratio. An improved signal to noise ratio allows detection of a reliable signal in the culture much sooner and therefore requires less time for the enrichment step.

The invention will be described in greater detail by way of specific examples. The following examples are offered for illustrative purposes, and are intended neither to limit nor define the invention in any manner.

EXAMPLE 1

Culturing a Novel Bacteriophage Using a Culture of *E. coli* as a Host

*E. coli* is cultured in liquid media using standard methods at room temperature or at an elevated temperature in a culture vessel, such as a flask, until the concentration of *E. coli* reaches a desired number. Examples of media commonly used to grow *E. coli* include Tryptic Soy Broth (TSB) and Brain Heart Infusion (BHI) broth. At the stage when the number of cells of *E. coli* is propagated to, for example, 2 to $3 \times 10^8$ per ml of the culture medium (e.g., OD=0.2), the bacteriophage is then added to the culture medium. After the bacteriophage has been added to the culture medium, the culture is maintained under substantially the same conditions as the previous culture in order to allow the *E. coli* to be infected with the bacteriophage resulting in replication and amplification of the bacteriophage and ultimately to lysis of the *E. coli* cells. As a consequence, when the culture is maintained for a predetermined period of time, a culture liquid of the bacteriophage in which there are few or no surviving *E. coli* is obtained. The culture liquid is then purified in accordance with conventional methods to remove *E. coli* cell debris, for example, by centrifugation or filtration through 0.45 µm to 0.2 µm filters, thereby yielding a sterile, clarified, liquid bacterial culture lysate containing the bacteriophage.

The bacteriophage according to the present invention may also be obtained from cultures of bacteria growing on solid or semi-solid agar culture media containing, for example, polypeptone and yeast extract, using standard methods well known to those skilled in the art. In this culture, it may be possible to use a two-layer agar culture medium with the layers having different agar concentrations. The culture using such a two-layer agar culture medium may be carried out by adding *E. coli* and phages to the upper, semi-solid layer and incubating the culture medium at room temperature or at elevated temperature. The resulting culture of the phages may then be processed by dissolving the semi-solid agar layer with a suitable liquid, such as liquid culture media, water, saline, buffer, or the like, and separating solid materials, e.g. cell debris, from the soluble phage by centrifugation or filtration, thereby yielding a clarified liquid containing high concentrations of the phage.

The surface of *E. coli* has a receptor configuration capable of absorbing a bacteriophage. Absorption, or binding, precedes the injection of the genes of the bacteriophage (DNA or RNA), into the *E. coli* cells. Once the phage genes are within the bacterial cell, they redirect the host cell metabolic processes to produce bacteriophage particles that accumulate until eventually the cell bursts open releasing progeny bacteriophage in the culture liquid.

In the culturing of some bacteriophage as described above, it is preferred to add a minute amount of a metal such as magnesium, manganese, calcium or the like to the culture medium for culturing the bacteria, such as *E. coli*. Suitable methods for isolating pure bacteriophage strains from a bacteriophage-containing sample are well known, and such methods may be adapted by the skilled artisan in view of the guidance provided herein. Isolation of bacteriophage from suitable samples typically proceeds by filtering the samples through a 0.45 µm or 0.25 µm filter to remove living organisms, mixing the filtrate with nutrient broth, inoculating the broth with a high concentration of a host bacterial strain, e.g., *E. coli*, and incubating to enrich the mixture with bacteriophage that can infect the host strain. After enrichment, the mixture is filtered to remove bacterial debris leaving lytic bacteriophage in the filtrate. Serial dilutions of the filtrate are plated on a confluent lawn of *E. coli*. bacteria, and the infection of a single bacterial cell by a single phage results in the production and release into the surrounding area, of many phage, which in turn infect and lyse neighboring bacteria. However, the agar limits the physical spread of the phage throughout the plate over a limited amount of time, resulting in small visibly clear areas called plaques where bacteriophage have destroyed the bacteria cells within the confluent lawn of bacterial growth. Since one plaque with a distinct morphology arose from one phage particle that replicated in bacteria within that area of the bacterial lawn, the purity of a bacteriophage preparation can be ensured by removing the material in that plaque with a sterile pasteur pipette, toothpick or similar device (a "plaque pick"), and using this material as the inoculum for further growth cycles of the phage. The bacteriophage produced in such cycles represent a single strain or "monophage." Each phage is uniquely identified by its size, structural morphology, protein composition, and genome sequence. Accordingly, the purity of a phage preparation (including confirmation that it is a monophage and not a polyvalent phage preparation) is assessed by a combination of techniques such as electron microscopy, SDS-PAGE, DNA restriction digest analysis, and analytical ultra centrifugation.

EXAMPLE 2

Use of Bacteriophage in Microbial Enrichment Media to Suppress Growth of Cross Reactive Organisms as a Means to Reduce the Occurrence of False Positive Results In the field of food pathogen testing it is common to test food samples for the presence of *Salmonella* bacteria. Methods for performing such tests include culturing a sample of food in a primary enrichment media that results in the replication of any *Salmonella* present along with other microorganisms in the sample. The resulting culture fluid is tested with a detection assay such as an immunoassay. It is known that some antibodies to *Salmonella* useful in such immunoassays exhibit cross reactivity to closely related microorganisms, like *Citrobacter* spp. (*J. Bacteriology,* 1978, 134(2), p. 462-469). Such cross reactivity can result in false positive responses. In cases where a detection assay exhibits cross reactivity it is useful to selectively inhibit the growth of cross-reactive organisms and thereby reduce the rate of false positive responses.

In this experiment, *Citrobacter freundii* and *Salmonella enteritidis* were grown individually in tryptic soy broth (TSB) for 18 hours at 37° C. Live cell counts for each culture were determined by standard dilution plating techniques. *C. freundii* specific phage FF2-20-1 (provided by Strategic Diagnostics Inc., Newark, Del.) samples were formulated to $10^7$ PFU/mL in TSB media. *C. freundii* culture was added to TSB media with and without the FF2-20-1 phage to final concentrations of 0, 1, 10, 100, 1000, 10,000, and 100,000 colony forming units per mL (cfu/mL). Each *C. freundii* treatment was co-inoculated with 0, 1, 10, and 100 cfu/mL *S. enteritidis*. All samples were incubated at 35° C. for 18 hours. Following the 18 hour incubation, all samples were tested with a lateral flow immunoassay (LFI) which specifically detects *C. freundii* and does not cross react with *S. enteritidis*. The higher the level of signal development (Color Card Result) on the LFI, the greater the concentration of *C. freundii*. Additionally, the concentrations of *S. enteritidis* and *C. freundii* in all treatments were determined by plating serial dilutions on a selective indicator media (ASAP Media, AES, Comborg, France) that can distinguish between *Salmonella* and *Citrobacter*.

The results of these experiments are summarized in Table 2 and demonstrate that addition of bacteriophage specific for *C. freundii* in the culture greatly reduces the concentrations of contaminating *C. freundii* bacteria in *S. enteritidis* cultures after an 18 hour incubation. In cultures that did not contain *Salmonella* or phage, the *Citrobacter* reached very high concentrations (approximately $10^8$ cfu/mL). A detection assay employing *Salmonella* antibodies exhibiting cross reactivity to *Citrobacter* would yield a false positive response to such a culture when there are no *Salmonella* present. The addition of specific phage to the enrichment prevents the growth of cross-reactive organisms thereby decreasing false positive responses.

EXAMPLE 3

Use of Bacteriophage in Microbial Enrichment Media as a Means of Enhancing the Productivity of the Target Organism and Decreasing False Negative Results

*Citrobacter freundii* and *Salmonella enteritidis* were grown individually in tryptic soy broth (TSB) for 18 hr at 37° C. Live cell counts for each culture were determined by standard dilution plating techniques. *C. freundii* specific phage FF2-20-1 (Strategic Diagnostics Inc.) samples were formulated to $1\times10^7$ PFU/mL in TSB media. *C. freundii* culture was added to TSB media with and without the FF2-20-1 phage to final concentrations of 0, 1, 10, 100, 1000, 10,000, and 100,000 cfu/mL. Each *C. freundii* treatment was co-inoculated with 0, 1, 10, and 100 cfu/mL *S. enteritidis*. All samples were incubated at 35° C. for 18 hours. Following the 18 hour incubation, the samples were tested with a lateral flow immunoassay (LFI) which detects *S. enteritidis* and does not cross react with *C. freundii*. The higher the level of signal development (Color Card Result) on the LFI, the greater the concentration of *Salmonella*. Additionally, *S. enteritidis* concentrations were determined by plating serial dilutions of all treatments onto ASAP Media selective agar (AES, Comborg, France).

The results of these experiments are summarized in Table 3 and demonstrate that the addition of bacteriophage specific for *C. freundii* greatly increases the productivity of *S. enteritidis* in cultures contaminated with *C. freundii* after an 18 hour incubation. Control cultures not treated with bacteriophage displayed reduced growth of *S. enteritidis* due to the presence of *C. freundii* contaminating the culture. In some cultures contaminated with *C. freundii*, the *Salmonella* concentration with phage was as high as $10^8$ cfu/mL while the *Salmonella* concentration in the corresponding cultures without phage was less than $10^3$ cfu/mL. Such a dramatic reduction in *Salmonella* productivity in the presence of competing microorganisms can lead to false negative results in detection assays. Addition of phage to the enrichment can improve target bacteria productivity and prevent false negative results.

TABLE 2

| | *S. enteritidis* Inoculation Level (cfu/mL) | | | | | | | |
|---|---|---|---|---|---|---|---|---|
| | 0 | | 1 | | 10 | | 100 | |
| *C. freundii* | *C. freundii* LFI Color Card Result | | | | | | | |
| Inoculation Level (cfu/mL) | Phage | No Phage | Phage | No Phage | Phage | No Phage | Phage | No Phage |
| 0 | 1 | 1 | 3 | 3 | 4 | 3 | 3 | 3 |
| 1 | 3 | 11 | 2 | 2 | 3 | 11 | 5 | 11 |
| 10 | 3 | 11 | 3 | 11 | 3 | 11 | 3 | 11 |
| 100 | 2 | 11 | 5 | 11 | 4 | 11 | 3 | 11 |
| 1000 | 2 | 11 | 5 | 11 | 5 | 11 | 4 | 11 |
| 10,000 | 3 | 11 | 3 | 11 | 5 | 11 | 5 | 11 |
| 100,000 | 10 | 11 | 11 | 11 | 11 | 11 | 11 | 11 |

| | *S. enteritidis* Inoculation Level (cfu/mL) | | | | | | | |
|---|---|---|---|---|---|---|---|---|
| | 0 | | 1 | | 10 | | 100 | |
| *C. freundii* | Resulting *C. freundii* Concentration (cfu/mL) | | | | | | | |
| Inoculation Level (cfu/mL) | Phage | No Phage | Phage | No Phage | Phage | No Phage | Phage | No Phage |
| 0 | <1E3 | <1E3 | <1E3 | <1E3 | <1E3 | <1E3 | <1E3 | <1E3 |
| 1 | <1E3 | 1.4E8 | <1E3 | <1E3 | <1E3 | 8.0E7 | <1E3 | 1.6E7 |
| 10 | <1E3 | 5.0E7 | <1E3 | 8.0E7 | <1E3 | 8.0E7 | <1E3 | 7.0E7 |
| 100 | <1E3 | 1.2E8 | <1E3 | 3.0E7 | <1E3 | 5.0E7 | <1E3 | 7.0E7 |
| 1000 | <1E3 | 4.0E7 | <1E3 | 5.0E7 | <1E3 | 1.1E8 | <1E3 | 8.0E7 |
| 10,000 | <1E3 | 1.9E8 | <1E3 | 2.7E8 | <1E3 | 2.6E8 | <1E3 | 1.3E8 |
| 100,000 | <1E3 | 2.9E8 | <1E3 | 1.4E8 | <1E3 | 8.0E7 | <1E3 | 3.5E8 |

TABLE 3

| | S. enteritidis Inoculation Level (cfu/mL) | | | | | | | |
|---|---|---|---|---|---|---|---|---|
| | 0 | | 1 | | 10 | | 100 | |
| C. freundii | | | S. enteritidis LFI Color Card Result | | | | | |
| Inoculation Level (cfu/mL) | Phage | No Phage | Phage | No Phage | Phage | No Phage | Phage | No Phage |
| 0 | 0 | 0 | 11 | 11 | 11 | 11 | 11 | 11 |
| 1 | 0 | 0 | 11 | 11 | 11 | 11 | 11 | 11 |
| 10 | 0 | 0 | 11 | 6 | 11 | 10 | 11 | 11 |
| 100 | 0 | 0 | 11 | 1 | 11 | 5 | 11 | 10 |
| 1000 | 0 | 0 | 11 | 2 | 11 | 5 | 11 | 9 |
| 10,000 | 0 | 0 | 0 | 1 | 11 | 3 | 11 | 6 |
| 100,000 | 0 | 0 | 11 | 1 | 11 | 2 | 11 | 6 |

| | S. enteritidis Inoculation Level (cfu/mL) | | | | | | | |
|---|---|---|---|---|---|---|---|---|
| | 0 | | 1 | | 10 | | 100 | |
| C. freundii | | | Resulting S. enteritidis Concentration (cfu/mL) | | | | | |
| Inoculation Level (cfu/mL) | Phage | No Phage | Phage | No Phage | Phage | No Phage | Phage | No Phage |
| 0 | <1E3 | <1E3 | 1.3E8 | 2.5E8 | 1.6E8 | 1.7E8 | 2.2E8 | 7.0E7 |
| 1 | <1E3 | <1E3 | 7.0E7 | 2.1E8 | 1.0E8 | 7.0E7 | 1.0E8 | 9.0E7 |
| 10 | <1E3 | <1E3 | 2.1E8 | <1E3 | 8.0E7 | 3.0E7 | 1.8E8 | 6.0E7 |
| 100 | <1E3 | <1E3 | 5.0E7 | <1E3 | 2.1E8 | 5.2E6 | 8.0E8 | 1.0E6 |
| 1000 | <1E3 | <1E3 | 8.0E7 | <1E3 | 1.1E8 | 8.0E5 | 2.3E8 | 1.8E6 |
| 10,000 | <1E3 | <1E3 | <1E3 | <1E3 | 3.2E8 | 1.0E5 | 2.2E8 | 2.2E6 |
| 100,000 | <1E3 | <1E3 | 2.1E8 | <1E3 | 3.5E8 | 5.0E5 | 1.3E8 | 1.2E6 |

EXAMPLE 4

Use of Bacteriophage to Reduce Enrichment Time and Increase Method Sensitivity

*Citrobacter freundii* (ATCC 9809) and *Salmonella enteritidis* were grown individually in tryptic soy broth (TSB) for 18 hr at 37° C. Live cell counts for each culture were determined by standard dilution plating techniques. *C. freundii* specific phage FF2-20-1 samples were formulated to $10^8$ pfu/mL in TSB media. *C. freundii* culture was added to TSB media with and without the FF2-20-1 phage to a final concentration of $10^5$ cfu/mL. Each *C. freundii* treatment was co-inoculated with 0, 0.02, 0.1, 2.0 and 10 cfu/mL *S. enteritidis*. All samples were incubated at 35° C. and were sampled periodically over a 24 hour period. At each sampling period, a sub-sample of each treatment was tested with a lateral flow immunoassay (LFI) which detects *S. enteritidis* and does not cross react with *C. freundii*. The higher the level of signal development (Color Card Result), on the LFI, the greater the concentration of *S. enteritidis*. Additionally, the concentration of *S. enteritidis* in all treatments were determined at 24 hours by plating serial dilutions on a selective indicator agar media (BGS Media, Difco).

TABLE 4

| Initial Phage Concentration (pfu/mL) | Initial† Salmonella Concentration (cfu/mL) | Replicate | Salmonella LFI Color Card Result at Sampling Time | | | | | | Ending Salmonella Concentration (cfu/mL) |
|---|---|---|---|---|---|---|---|---|---|
| | | | 3 hr | 6 hr | 9 hr | 12 hr | 15 hr | 24 hr | 24 hr |
| 0 | 0 | 1 | — | — | — | — | — | — | $<10^5$ |
| | | 2 | — | — | — | — | — | — | $<10^5$ |
| | | 3 | — | — | — | — | — | — | $<10^5$ |
| | 0.02 | 1 | — | — | — | — | — | — | $<10^5$ |
| | | 2 | — | — | — | — | — | — | $<10^5$ |
| | | 3 | — | — | — | — | — | — | $<10^5$ |
| | 0.1 | 1 | — | — | — | — | — | — | $<10^5$ |
| | | 2 | — | — | — | — | — | — | $<10^5$ |
| | | 3 | — | — | — | — | — | — | $<10^5$ |
| | 2 | 1 | — | — | — | — | 1 | 9 | $4 \times 10^7$ |
| | | 2 | — | — | — | — | 0.5 | 9 | $3 \times 10^7$ |
| | | 3 | — | — | — | — | 1 | 9 | $1 \times 10^7$ |
| | 10 | 1 | — | — | — | 0.5 | 2 | 11 | $8 \times 10^7$ |
| | | 2 | — | — | — | 0.5 | 2 | 11 | $9 \times 10^7$ |
| | | 3 | — | — | — | 0.5 | 3 | 11 | $8 \times 10^7$ |
| $10^8$ | 0 | 1 | — | — | — | — | — | — | $<10^5$ |
| | | 2 | — | — | — | — | — | — | $<10^5$ |
| | | 3 | — | — | — | — | — | — | $<10^5$ |
| | 0.02 | 1 | — | — | — | 1 | 11 | 6 | $3.1 \times 10^8$ |

TABLE 4-continued

| Initial Phage Concentration (pfu/mL) | Initial† Salmonella Concentration (cfu/mL) | Replicate | Salmonella LFI Color Card Result at Sampling Time | | | | | | Ending Salmonella Concentration (cfu/mL) |
|---|---|---|---|---|---|---|---|---|---|
| | | | 3 hr | 6 hr | 9 hr | 12 hr | 15 hr | 24 hr | 24 hr |
| | | 2 | — | — | — | 1 | 11 | 6 | $4.1 \times 10^8$ |
| | | 3 | — | — | — | 1 | 11 | 9 | $2.2 \times 10^8$ |
| | 0.1 | 1 | — | — | — | 2 | 11 | 9 | $4.4 \times 10^8$ |
| | | 2 | — | — | — | 2 | 11 | 9 | $4.5 \times 10^8$ |
| | | 3 | — | — | 4 | 11 | 9 | | $4.0 \times 10^8$ |
| | 2 | 1 | — | — | 2 | 11 | 11 | 6 | $8.5 \times 10^8$ |
| | | 2 | — | — | 4 | 11 | 11 | 6 | $1.3 \times 10^9$ |
| | | 3 | — | — | 4 | 11 | 11 | 6 | $1.1 \times 10^9$ |
| | 10 | 1 | — | — | 8 | 11 | 11 | 7 | $8.3 \times 10^8$ |
| | | 2 | — | — | 7 | 11 | 11 | 7 | $1.3 \times 10^9$ |
| | | 3 | — | — | 8 | 11 | 11 | 7 | $1.1 \times 10^9$ |

†All treatment groups contained a starting concentration of $10^5$ cfu/mL *C. freundii* at the time of *S. enteritidis* inoculation.

The results of these experiments are summarized in Table 4, above, and demonstrate that the presence of bacteriophage to *C. freundii* in cultures containing both *C. freundii* and very low concentrations of *S. enteritidis* results in a significant reduction in the amount of enrichment time required to detect *Salmonella*. Similarly, the presence of *C. freundii* phage resulted in improved sensitivity. With phage, *Salmonella* cultures containing starting concentrations of 0.02 cfu/mL were readily detected while without phage, the lowest starting *Salmonella* concentration that was detected was 2 cfu/mL. Without the phage, two treatment groups, containing 0.02 and 0.1 cfu/mL *S. enteritidis*, never reached detectable concentrations using the LFI and therefore are falsely negative. Addition of the phage reduced the number of false negative responses using the LFI detection method.

EXAMPLE 5

Use of Bacteriophage to Reduce False Positive Results When Detecting *Salmonella* in Beef Twenty five gram samples of beef (35) were enriched in 225 mL RapidChek media (Strategic Diagnostics Inc.) at 42° C. for 24 hours. An additional set of 35 beef samples were enriched under similar conditions in RapidChek *Salmonella* media supplemented with a cocktail of five phage specifically targeting *E. coli* and *Citrobacter* spp.

*E. coli* and *Citrobacter* are common microbiological contaminants of beef, are structurally very closely related to *Salmonella*, and frequently cross react with antibodies directed towards *Salmonella* antigens employed in immunoassays to detect *Salmonella* in food. The five phage used in this example were specifically selected to lyse *E. coli* and *Citrobacter* spp. that cross react with *Salmonella* antibodies.

At 24 hours, all samples were tested using a Lateral Flow Immunoassay (LFI) for the detection of *Salmonella* spp. In addition, all samples were streaked to Brilliant Green Sulfa Agar (BGS) and Xylose Lysine Tergitol 4 Agar (XLT4) for the selective detection of *Salmonella* spp. and incubated for 48 hours at 37° C.

Thirteen of 35 samples were reported as LFI positive from the non-phage treatment, none of which were confirmed as positive using cultural methodology (XLT4 and BGS plates). No positive LFI results were reported from the samples enriched using the phage-supplemented RapidChek media nor were any of these samples positive using cultural methods. Thus, there were 13 of 35 false positive results without the phage and none with the phage.

EXAMPLE 6

Improved Specificity of Biochemical Tests for Detection of Coliforms in Water

Coliforms are a general class of bacteria that inhabit the intestinal tract of man and other animals and utilize the enzyme beta-D-galactosidase to ferment the sugar lactose. Although some coliforms are found in the intestinal tract of man, most are found throughout the environment and have little sanitary significance (Greenberg, A. E. and Hunt, D. A. (Eds.) 1985. LABORATORY PROCEDURES FOR THE EXAMINATION OF SEAWATER AND SHELLFISH, $5^{th}$ ed. The American Public Health Association, Washington, D.C.). Fecal coliforms are members of the total coliform group of bacteria. They are characterized by their ability to ferment lactose at 112.1° F. (44.5° C.) and are considered more specific indicators of fecal contamination than are coliforms that ferment lactose only at 95° F. (35°). *E. coli* and some *Klebsiella pneumoniae* strains are the principal fecal coliforms (THE DRINKING WATER DICTIONARY, Copyright©2000, American Water Works Association).

A number of commercial products are available for the detection of coliforms that rely on the enzyme beta-D-galactosidase to convert a colorless substrate to a colored or fluorescent molecule, or cause other biochemical reactions such as gas formation, and thereby indicate the presence of coliforms in a water sample. Examples of such products are Colilert® from IDEXX Laboratories, Inc., Westbrook, Me.; Colitag™, CPI International, Santa Rosa, Calif.; m-ColiBlue24® from Hach Company, Loveland, Colo.; ColiGel™, E*Colite™ and PathoGel™ from Charm Sciences, Inc. Malden, Mass.; Colifast®, Oslo, Norway; Coli-Trak®, BioControl Systems, Inc., Bellevue, Wash.; and others.

A limitation of these techniques is that bacteria other than coliforms express beta-D-galactosidase and cause false positive results. For example, the Trouble-Shooting Guide for the m-ColiBlue24 product from Hach Company states that the false positive rate for the total coliforms test is 26.8% due to the presence in water samples of known beta-D-galactosidase positive bacteria that are not coliforms. Similarly, a number of marine bacteria cause false positive results in such tests, including *Vibrio* spp., and therefore their use for testing quality of marine water is limited (J. M. Pisciotta, et al., 2002. *Applied and Environmental Microbiology*, 68(2), p. 539-544).

Bacteriophage, as described herein, reactive to bacteria known to cause false positive results in such biochemical tests, can be incorporated into the test to prevent or reduce the growth of such bacteria and thereby reduce false positive reactions. Many such tests are known to those skilled in the art, including but not limited to water tests such as Enterolert™, IDEXX Laboratories, Inc., and microbiological media, including chromogenic media, such as those contained within the DIFCO MANUAL (11$^{th}$ edition, 1998, Difco Laboratories, Division of Becton Dickinson and Company, Sparks, Md.), all of which are included by reference herein. Such biochemical tests can be used for enumeration, characterization, identification, classification, or isolation of microorganisms in any field of work including but not limited to food, water and air testing, medical diagnostics, veterinary diagnostics, agricultural and environmental tests, industrial, commercial and pharmaceutical processes, product quality and the like.

EXAMPLE 7

Improved Specificity of a Test Method for Fecal Coliforms in Water Samples by Bacteriophage A culture of the non-fecal coliform bacteria *Klebsiella oxytoca* (Strategic Diagnostics Inc.) was streaked onto a TSA (Difco) plate and incubated over night at 37° C. A single colony isolate was transferred to 10 mL TSB (Difco) and incubated over night at 37° C. Ten-fold serial dilutions of the *K. oxytoca* TSB culture were prepared in peptone water (Difco). Bacteriophage Kss3.2-5 (Strategic Diagnostics Inc.) infects *K. oxytoca* resulting in bacterial lysis. Fifty mL of Kss3.2-5 phage solution at a concentration of $10^7$ pfu/mL was prepared in sterile distilled water. Colilert tubes for the detection of coliforms in water were purchased from IDEXX Laboratories. Five Colilert tubes were reconstituted with 10 mL of the phage solution and five Colilert tubes were reconstituted with 10 mL of sterile distilled water. All tubes were mixed until the powdered reagent was dissolved. One mL of the $10^{-5}$, $10^{-6}$, $10^{-7}$, and $10^{-8}$ bacterial dilutions was mixed into the individual Colilert tubes with and without phage. One mL of peptone water was added to two tubes and served as negative controls. All of the tubes were incubated at 37° C. for 18 hours according to the manufacturer's specification.

*K. oxytoca* produced clear positive results in the Colilert assay indicating the presence of a coliform, however, *K. oxytoca* is not a fecal coliform and therefore the results are insufficient for indicating the presence of fecal contamination and potentially pathogenic bacteria in the sample. In the presence of phage, all dilutions tested of this bacteria culture produced negative results improving the specificity of the test for fecal coliforms.

EXAMPLE 8

Reduction in False Positive Responses in a Test Method for Total Coliforms in Water Samples by Bacteriophage

*Aeromonas veronii* (American Type Culture Collection, ATCC 51106), a non-coliform bacteria, was grown for 6 hours at 30° C. in TSB from a single colony isolate. The TSB culture was diluted by a factor of ten in peptone water. Four Colilert (IDEXX Laboratories) tubes were rehydrated with sterile, de-ionized water. One mL of the diluted *A. veronii* culture was inoculated into duplicate Colilert tubes. Two additional tubes were inoculated with 1 mL peptone water as negative controls. One of the *A. veronii* tubes and one of the negative control tubes received $10^7$ pfu/mL (final concentration) of the Aeromonas phage 15-11 (Strategic Diagnostics Inc.) in TSB media. The other set received the same volume of TSB media without phage. Tubes were incubated over night at 37° C. according to the manufacturer's specification. Following incubation, the *A. veronii* tube without the phage had turned bright yellow, falsely indicating the presence of a coliform. The *A. veronii* tube without the phage remained colorless indicating a negative response. Therefore, the presence of the bacteriophage eliminated the false positive response produced by the *A. veronii* in the assay.

EXAMPLE 9

Novel Bacteriophage Compositions and Methods for Enumeration of Target Bacteria

In this example it is envisioned that an agar media used for the detection and enumeration of coliform bacteria could be made more specific for the detection and enumeration of fecal coliforms by minimizing the growth of non-fecal coliforms using specific phage incorporated within solid or semi-solid media.

MI Agar (Difco) used for the detection of coliform bacteria, was prepared by rehydrating the medium as directed by the manufacturer, boiled for one minute and cooled to 50° C. *Klebsiella* phage kss3.2-5 (Strategic Diagnostics Inc.) was then added to half of the molten agar media at a final concentration of $2.6 \times 10^8$ plaque forming units per mL (pfu/mL). Five mL aliquots of molten MI agar with and without phage were then overlaid onto plates containing trypticase soy agar (TSA) and cooled to room temperature. *Klebsiella oxytoca* strain 1055-1, a non-fecal coliform, was grown in trypticase soy broth (TSB) for 18 h at 37° C. Ten-fold serial dilutions of the *K. oxytoca* culture were prepared in peptone water and the $10^{-8}$ and $10^{-9}$ dilutions were applied to the surface of both of the solidified MI agar treatments and incubated at 37° C. for 18 h. Bacterial colonies were counted under UV light source to discern coliforms according to the manufacturer's instructions. The data demonstrate that the incorporation of the phage into the solidified agar media results in a reduction in the number of non-coliform bacteria.

| Phage | *Klebsiella oxytoca* dilution | | | | |
|---|---|---|---|---|---|
| | $10^{-5}$ | $10^{-6}$ | $10^{-7}$ | $10^{-8}$ | none |
| Without | +++ | +++ | +++ | +++ | − |
| With | − | − | − | − | − |

| *K. oxytoca* dilution applied to plate | Number of Colonies | |
|---|---|---|
| | MI Agar | MI Agar w/phage |
| $10^{-8}$ | 66 | 0 |
| $10^{-9}$ | 11 | 0 |

EXAMPLE 10

New Bacteriophage Compositions and Methods of Enumerating Fecal Coliforms

In this example the use of phage to enhance the specificity of a method from a general coliform enumeration method to a fecal coliform enumeration method is demonstrated. *E. coli* strain 4157, a fecal coliform, was grown in trypticase soy broth (TSB) at 37° C. for 18 hours and serially diluted in phosphate buffered saline (PBS) (Sigma). Additionally, *Klebsiella oxytoca* strain 1055-1, a non-fecal coliform, was grown on trypticase soy agar (TSA) at 37° C. for 18 hours and serially diluted in PBS. Thirty Colilert tubes for the detection of coliform bacteria (IDEXX Laboratories) were rehydrated with sterile tap water. One hundred microliters (100 uL) of a $10^{-8}$ dilution of the *E. coli* culture was added to each of the 30 tubes. In addition, 100 uL of the $10^{-6}$ *Klebsiella* dilution was added to each of 20 tubes. Lastly, 100 uL of *Klebsiella* phage kss3.2-5 (Strategic Diagnostics Inc.) diluted in PBS was added to a final concentration of $10^8$ plaque forming units per mL to 10 of the tubes containing both *E. coli* and *K. oxytoca*. All tubes were capped, mixed and incubated at 37° C. for 18 hours. Tubes were evaluated after 18 hours for the presence of yellow color indicating the presence of coliform bacteria. The number of positive tubes was used to calculate the most probable number (MPN) of bacteria (Blodgett, R. 1998; Update January 2001; Appendix 2; Most Probably Numbers from Serial Dilutions. In: US Food, Drug and Administration, Center for Food Safety and Applied Nutrition, Bacteriological Analytical Manual. Edition 8, Revision A/1998), using the tables supplied in the Coilert product User's Guide. The media composition containing bacteriophage resulted in a new method with improved specificity for enumeration of fecal coliforms. The addition of the phage effectively eliminated the non-fecal coliform *K. oxytoca* from the analysis thereby enabling the enumeration of just the fecal coliform, *E. coli*.

| Treatment | # of Total Tubes | # of Positive Tubes | MPN index/100 mL |
|---|---|---|---|
| *E. coli* | 10 | 3 | 3.6 |
| *E. coli* + *K. oxytoca* | 10 | 10 | >23.0 |
| *E. coli* + *K. oxytoca* + Phage kss3.2-5 | 10 | 3 | 3.6 |

Although methods and materials similar or equivalent to those described herein can be used in the practice or testing of the present invention, suitable methods and materials are described above. All publications, patent applications, patents and other cited references mentioned herein are incorporated by reference in their entirety. In addition, the materials, methods, and examples are illustrative only and not intended to be limiting.

The foregoing description is provided for describing various embodiments relating to the invention. Various modifications, additions and deletions may be made to these embodiments and/or structures without departing from the scope and spirit of the invention.

What is claimed is:

1. A method for detecting a target microorganism in a sample containing non-target bacteria comprising:
    forming a reaction mixture by combining the sample with a nutrient media and a bacteriophage composition comprising bacteriophage specific for the non-target bacteria in the sample, wherein the non-target bacteria compete with the target microorganism for nutrients in the media, and wherein the bacteriophage lyses the non-target bacteria in the sample without lysing the target microorganism, thereby reducing the occurrence of a false negative detection result by inhibiting growth of competing microorganisms while allowing the target to grow in the media, and
    detecting the target microorganism.

2. The method of claim 1 further comprising incubating the reaction mixture for a sufficient amount of time to allow lysis of the non-target bacteria in the sample and a growth in the number of target bacteria to detectable levels.

3. The method of claim 1 wherein the bacteriophage composition comprises two or more bacteriophages specific for different non-target bacteria.

4. The method of claim 1 wherein the target microorganism is a bacteria.

5. The method of claim 1 wherein the bacteriophage composition comprises a bacteriophage that lyses gram negative bacteria.

6. The method of claim 1 wherein the target microorganism is *Salmonella* and the bacteriophage composition comprises a bacteriophage specific for lysis of *E. coli* or *Citrobacter*.

7. The method of claim 1 wherein the target microorganism is *Salmonella* and the bacteriophage composition comprises a first bacteriophage specific for lysis of *E coli* and a second bacteriophage specific for lysis of *Citrobacter*.

8. The method of claim 1 wherein the reaction mixture further comprises an antibiotic.

9. The method of claim 8 wherein the antibiotic inhibits the growth of gram positive bacteria.

10. The method of claim 1 wherein the target microorganism is detected using a chemical, enzyme, nucleic acid molecule or antibody.

11. The method of claim 1 wherein the bacteriophage composition reduces the growth of non-target bacteria that cross-react with a detection reagent used to detect the target microorganism, thereby reducing the occurrence of false positive detection results.

12. The method of claim 1 wherein the bacteriophage composition enhances detection sensitivity.

13. The method of claim 1 wherein the bacteriophage composition inhibits growth of competing microorganisms thereby shortening the amount of time needed to allow a growth in the number of target bacteria to detectable levels.

14. The method of claim 1, wherein the sample is an industrial, biological, food, pharmaceutical, commercial, or fermentation sample.

15. The method of claim 1, wherein the bacteriophage composition improves yield of the target microorganism.

16. The method of claim 1, wherein the bacteriophage composition is a liquid or is in a solid or semi-solid substrate.

17. A method for detecting a target microorganism in a sample containing non-target bacteria comprising:
    forming a reaction mixture by combining the sample with a bacteriophage composition comprising bacteriophage specific for the non-target bacteria in the sample, wherein the non-target bacteria in the sample cross-react with a detection reagent used to detect the target microorganism, and wherein the bacteriophage lyses the non-target bacteria without lysing the target microorganism, thereby reducing the occurrence of a false positive detection result, and
    detecting the target microorganism.

18. The method of claim 17, further comprising incubating the reaction mixture for a sufficient amount of time to allow lysis of the non-target bacteria in the sample and a growth in the number of target bacteria to detectable levels.

19. The method of claim 17, wherein the bacteriophage composition comprises two or more bacteriophages specific for different non-target bacteria.

20. The method of claim 17, wherein the target microorganism is a bacteria.

21. The method of claim 17, wherein the bacteriophage composition comprises a bacteriophage that lyses gram negative bacteria.

22. The method of claim 17, wherein the target microorganism is *Salmonella* and the bacteriophage composition comprises a bacteriophage specific for lysis of *E. coli* or *Citrobacter*.

23. The method of claim 17, wherein the target microorganism is *Salmonella* and the bacteriophage composition comprises a first bacteriophage specific for lysis of *E. coli* and a second bacteriophage specific for lysis of *Citrobacter*.

24. The method of claim 17, wherein the reaction mixture further comprises an antibiotic.

25. The method of claim 24, wherein the antibiotic inhibits the growth of gram positive bacteria.

26. The method of claim 17, wherein the target microorganism is detected using a chemical, enzyme, nucleic acid molecule, or antibody.

27. The method of claim 17, wherein the bacteriophage composition enhances detection sensitivity.

28. The method of claim 17, wherein the bacteriophage composition inhibits growth of competing microorganisms thereby shortening the amount of time needed to allow a growth in the number of target bacteria to detectable levels.

29. The method of claim 17, wherein the sample is an industrial, biological, food, pharmaceutical, commercial, or fermentation sample.

30. The method of claim 17, wherein the bacteriophage composition improves yield of the target microorganism.

31. The method of claim 17, wherein the bacteriophage composition is a liquid or is in a solid or semi-solid substrate.

* * * * *